(12) United States Patent
Yan et al.

(10) Patent No.: US 10,980,850 B2
(45) Date of Patent: Apr. 20, 2021

(54) USE OF IAP INHIBITOR AND ONCOLYTIC VIRUS IN PREPARATION OF ANTI-TUMOR DRUG

(71) Applicant: Guangzhou Virotech Pharmaceutical Co., Ltd., Guangdong (CN)

(72) Inventors: Guangmei Yan, Guangzhou (CN); Jing Cai, Guangzhou (CN); Yuan Lin, Guangzhou (CN); Haipeng Zhang, Guangzhou (CN); Suizhen Lin, Guangzhou (CN); Shoufang Gong, Guangzhou (CN); Jun Hu, Guangzhou (CN); Xiao Xiao, Guangzhou (CN); Kai Li, Guangzhou (CN); Jiankai Liang, Guangzhou (CN); Yaqian Tan, Guangzhou (CN); Wenbo Zhu, Guangzhou (CN); Wei Yin, Guangzhou (CN)

(73) Assignee: Guangzhou Virotech Phamaceutical Co., Ltd., Guangdong (CN)

( * ) Notice: Subject to any disclaimer, the term of this patent is extended or adjusted under 35 U.S.C. 154(b) by 0 days.

(21) Appl. No.: 16/325,974

(22) PCT Filed: Aug. 18, 2017

(86) PCT No.: PCT/CN2017/097972
§ 371 (c)(1),
(2) Date: Feb. 15, 2019

(87) PCT Pub. No.: WO2018/033129
PCT Pub. Date: Feb. 22, 2018

(65) Prior Publication Data
US 2019/0167737 A1    Jun. 6, 2019

(30) Foreign Application Priority Data
Aug. 18, 2016    (CN) .......................... 201610688097.9

(51) Int. Cl.
| | | |
|---|---|---|
| *A61K 35/768* | (2015.01) | |
| *A61K 31/427* | (2006.01) | |
| *A61K 31/404* | (2006.01) | |
| *A61K 9/00* | (2006.01) | |
| *A61K 9/19* | (2006.01) | |
| *A61K 9/48* | (2006.01) | |
| *A61K 9/70* | (2006.01) | |
| *A61P 35/00* | (2006.01) | |
| *A61K 31/713* | (2006.01) | |
| *A61K 45/06* | (2006.01) | |

(52) U.S. Cl.
CPC .......... *A61K 35/768* (2013.01); *A61K 9/0019* (2013.01); *A61K 9/19* (2013.01); *A61K 9/48* (2013.01); *A61K 9/7023* (2013.01); *A61K 31/404* (2013.01); *A61K 31/427* (2013.01); *A61K 31/713* (2013.01); *A61K 45/06* (2013.01); *A61P 35/00* (2018.01)

(58) Field of Classification Search
CPC ...... A61K 35/768; A61K 9/0019; A61K 9/19; A61K 9/48; A61K 9/7023; A61K 31/404; A61K 31/427; A61P 35/00
See application file for complete search history.

(56) References Cited

U.S. PATENT DOCUMENTS

| | | |
|---|---|---|
| 2005/0197403 A1 | 9/2005 | Harran et al. |
| 2008/0020986 A1 | 1/2008 | Condon et al. |
| 2009/0175826 A1 | 7/2009 | Subbiah et al. |
| 2010/0247622 A1 | 9/2010 | Coffey et al. |
| 2016/0143995 A1 | 10/2016 | Pellegrini |
| 2017/0304380 A1 | 10/2017 | Yan et al. |

FOREIGN PATENT DOCUMENTS

| | | | |
|---|---|---|---|
| CN | 1926118 | A | 3/2007 |
| CN | 101516904 | A | 8/2009 |
| CN | 101820892 | A | 9/2010 |
| CN | 102050867 | A | 5/2011 |
| CN | 102796709 | A | 11/2012 |
| CN | 102813939 | A | 12/2012 |
| CN | 103055325 | A | 4/2013 |
| CN | 104814984 | * | 8/2015 |
| CN | 104814984 | A | 8/2015 |
| CN | 105451726 | A | 3/2016 |
| CN | 105456302 | A | 4/2016 |
| CN | 106265764 | A | 1/2017 |
| WO | 2015109391 | A1 | 7/2015 |
| WO | WO 2015/109391 | * | 7/2015 |
| WO | 2018/033129 | A1 | 2/2018 |

OTHER PUBLICATIONS

Putt et al. Nature Chemical Biology 2, 543-550 (2006) (Year: 2006).*
Hu et al. in Cell Cycle 8(20), 3328-3339 (2009) (Year: 2009).*
Glioma vs Glioblastoma at https://www.neurosurgeonsofnewjersey.com/glionna-vs-glioblastoma/ (retrieved from the internet Apr. 7, 2020) (Year: 2020).*
Species Specific Information_Mouse http://web.jhu.edu/animal care/procedures/mouse.html (retrieved from the internet Apr. 7, 2020) (Year: 2020).*
Wen et al.in Virus Genes 35:597-603 (2007) (Year: 2007).*
Ying et al. in Nature Medicine 5(7), 823-827 (1999) (Year: 1999).*
Communication, dated Jul. 22, 2019, with extended European search report, issued by the European Patent Office in European Application No. 17841101.3.

(Continued)

*Primary Examiner* — Dennis Heyer
(74) *Attorney, Agent, or Firm* — Sughrue Mion, PLLC

(57) ABSTRACT

Described herein is use of a Caspase activator and an oncolytic virus in the preparation of an anti-tumor drug. As described, Caspase activator can enhance the anti-tumor effect of oncolytic virus, and the combination of Caspase activator and oncolytic virus produces a significant synergistic anti-tumor effect, and demonstrates an effective therapy for the treatment of tumors that are less sensitive to other pharmaceutical treatments.

13 Claims, 5 Drawing Sheets

Specification includes a Sequence Listing.

(56) References Cited

OTHER PUBLICATIONS

Yuan Lin et al., "Identification and characterization of alphavirus M1 as a selective oncolytic virus targeting ZAP-defective human cancers", Proceedings of National Academy of Sciences, vol. 111 No. 42, Oct. 6, 2014, pp. E4504-E4512 * E4510, left column*.

Shavvn T. Beug et al., "Combinatorial cancer immunotherapy strategies with proapoptotic small-molecule IAP antagonists", International Journal of Developmental Biology, vol. 59, No. 1-2-3, Jan. 1, 2015, pp. 141-147. * p. 142-p. 143 *.

Shavvn T. Beug et al., "Smac mimetics and innate immune stimuli synergize to promote tumor death", Nature Biotechnology, vol. 32 No. 2, Feb. 1, 2014, pp. 182-192. * Figure 1 *.

Qiuwei Pan et al., "Synergistic antitumor activity of XIAP-shRNA and TRAIL expressed by oncolytic adenoviruses in experimental HCC", Acta Oncologica vol. 47 No. 1, Jan. 8, 2008, pp. 135-144. * the whole document *.

Shawn T. Beug, et al., "Smac mimetics and innate immune stimuli synergize to promote tumor death", Nature Biotechnology, Feb. 2014, 11 pages, vol. 32, No. 2.

Shawn T. Beug, et al., "Smac mimetics combined with innate immune stimuli create the perfect cytokine storm to kill tumor cells", OncoImmunology 3, Apr. 2014, pp. e28541-1 to e28541-3, Landes Bioscience.

Jin-Sheng Wen, et al., "Genomic analysis of a Chinese isolate of Getah-like virus and its phylogenetic relationship with other Alphaviruses", Virus Genes, 2007, pp. 597-603, vol. 35.

Rama Rathore, et al., "Overcoming chemotherapy drug resistance by targeting inhibitors of apoptosis proteins (IAPs)", Apoptosis, Apr. 19, 2019, pp. 898-919, vol. 22.

Sean P. Dineen, et al., "Smac Mimetic Increases Chemotherapy Response and Improves Survival in Mice with Pancreatic Cancer", Cancer Research, Mar. 2010, pp. 2852-2861, vol. 70, No. 7.

China Office Action for Application No. 201610688097.9 dated Mar. 8, 2017.

China Office Action for Application No. 201610688097.9 dated Dec. 14, 2017.

Taiwan Office Action for Application No. 106128177 dated May 8, 2018.

Taiwan Office Action for Application No. 106128177 dated Nov. 13, 2018.

International Search Report for PCT/CN2017/097972 dated Nov. 2, 2017 [PCT/ISA/210].

Written Opinion for PCT/CN2017/097972 dated Nov. 2, 2017 [PCT/ISA/237].

Non-Final Notice of Decision of Refusal of corresponding Japanese Application (Application No. 2019-509464), dated Mar. 24, 2020 * The Whole Document *.

R. G. Korneluk, "Smac mimetics combined with innate immune stimuli: new tools to kill tumor cells", vol. 76, Nov. 30, 2015, p. 61, ID 261 * The Whole Paragragh *.

Communication, dated May 12, 2020, issued by the European Patent Office in counterpart European Patent Application No. 17 841 101.3.

* cited by examiner

US 10,980,850 B2

USE OF IAP INHIBITOR AND ONCOLYTIC VIRUS IN PREPARATION OF ANTI-TUMOR DRUG

CROSS REFERENCE TO RELATED APPLICATIONS

This application is a National Stage of International Application No. PCT/CN2017/097972, filed on Aug. 18, 2017, which claims priority from Chinese Patent Application No. 201610688097.9, filed Aug. 18, 2016, the contents of which are incorporated by referenced herein in their entirety.

FIELD

The present disclosure relates to the field of biomedicine, and particularly to therapeutic combinations of a Caspase activator and an oncolytic virus and uses thereof in anti-tumor treatments.

BACKGROUND

Oncolytic virus is a class of replicatable viruses that infect and kill tumor cells. Some oncolytic viruses can selectively infect cancer cells over normal cells with little or no infection of normal cells. Some oncolytic viruses can infect cancer cells and normal cells, but exhibit greater or faster lethality against the cancer cells. Oncolytic virotherapy, is an innovative strategy for targeted tumor therapy, which utilizes a natural or genetically modified virus (or combination thereof) to infect tumor cells, in which the virus then replicates with the effect of dissolving and killing the tumor cells, preferably in a targeted way, and preferably with little or no damage to normal cells.

One example of an oncolytic virus is the M1 virus (Alphavirus M1), which belongs to Alphavirus sp., and is recognized as an effective anti-tumor drug. For example, Chinese patent application 201410425510.3 discloses that M1 virus can selectively kill tumor cells without affecting the survival of normal cells. Despite its proven efficacy, different tumors show different sensitivity to M1 virus. For certain tumors, M1 virus, when administered alone, does not exhibit a satisfactory oncolytic effect. According to the Chinese patent application No. 201410425510.3, incorporated herein by reference for its discussion of treatment of tumors with M1 virus and other viruses and for its discussion of different outcomes for different tumor types and treatment levels/methodologies, it is disclosed that M1 present different efficacy when treating different tumor types. When used for treating pancreatic cancer, nasopharyngeal carcinoma, prostate cancer and melanoma, it presents a most effective result. When used for treating colorectal cancer, liver cancer, bladder cancer and breast cancer, it is less effective than the previous mentioned type. When used for treating glioma, cervical cancer, lung cancer, it is even less effective. When used for treating gastric cancer, it presents a least effective result.

In a previous patent application (Chinese Patent application No. 201510990705.7), it is disclosed that chrysophanol and its derivatives can be used as anti-tumor synergists for M1 virus, and a combination of both could reduce the survival rate of tumor cells to 39.6%. However, there is still much progress to be made in developing therapeutic combinations that include an oncolytic virus. Disclosed herein is an anti-tumor synergist for oncolytic virus, which could produce an increased anti-tumor effect.

SUMMARY

Provided herein are synergistic anti-tumor therapies that include a Caspase activator and an oncolytic virus, such as an oncolytic alphavirus.

Also provided is a use of a Caspase activator in the preparation of an anti-tumor synergist for oncolytic virus.

Also provided is an anti-tumor pharmaceutical composition that enables oncolytic virus to exhibit better anti-tumor effect, by its use in combination with a Caspase activator.

Also provided is a synergistic anti-tumor drug combination with oncolytic virus, and which is preferably directed to tumors that are not sensitive to oncolytic virus.

Also provided are methods of treatment of a solid or hematological (i.e. blood) tumor that include administration of the foregoing therapeutic combinations.

The foregoing and other objects, features, and advantages will become more apparent from the following detailed description, which proceeds with reference to the accompanying figures.

BRIEF DESCRIPTION OF THE DRAWINGS

Throughout the drawings, the following abbreviations are used: LCL161: LCL161 treatment group; Brirnapant: Brirnapant treatment group: M1+LCL161: a combined treatment group using M1 virus and LCL161; M: a group treated with M1 virus alone; M+L: a combined treatment group using M1 virus and LCL161.

FIG. 2(A): Survival rate of HCT116 cells treated with M1 alone, LCL161, or a combination of M1 and LCL161. FIG. 2(B): Survival rate of HCT116 cells treated with M1 alone, Birinapant, or a combination of M1 and Birinapant. Also shown is the survival rate of SW620 cells (FIGS. 2(C) and 2(D)), Huh7 cells (FIGS. 2(E) and 2(F)), and PLC cells (FIGS. 2(G) and 2(H)) following single and combined treatment with M1 and LCL161 or Birinapant.

FIGS. 3(A) and 3(B): Western blot detection of cIAP1 and cIAP2. FIGS. 3(C) and 3(D) show results of MTT assays demonstrating anti-cancer cell efficacy of combined cIAP1 or cIAP2 inhibition and M1 infection.

FIG. 4(A) presents quantitation of tumor volume over time in response to the indicated treatments. FIG. 4(B) shows shrinkage in the tumor size in response to the indicated treatments.

FIGS. 5(A) and 5(B) are charts showing the observed activity of Caspase 3/7 in HCT116 (FIG. 5A) and Huh7 (FIG. 5B) cells. FIGS. 5(C) and 5(D) are charts showing the observed activity of Caspase 8 in HCT116 (FIG. 5C) and Huh7 (FIG. 5D) cells. FIGS. 5(E) and 5(F) are charts showing the observed activity of Caspase 9 in HCT116 (FIG. 5E) and Huh7 (FIG. 5F) cells.

BRIEF DESCRIPTION OF THE DESCRIBED SEQUENCES

Figure 1:
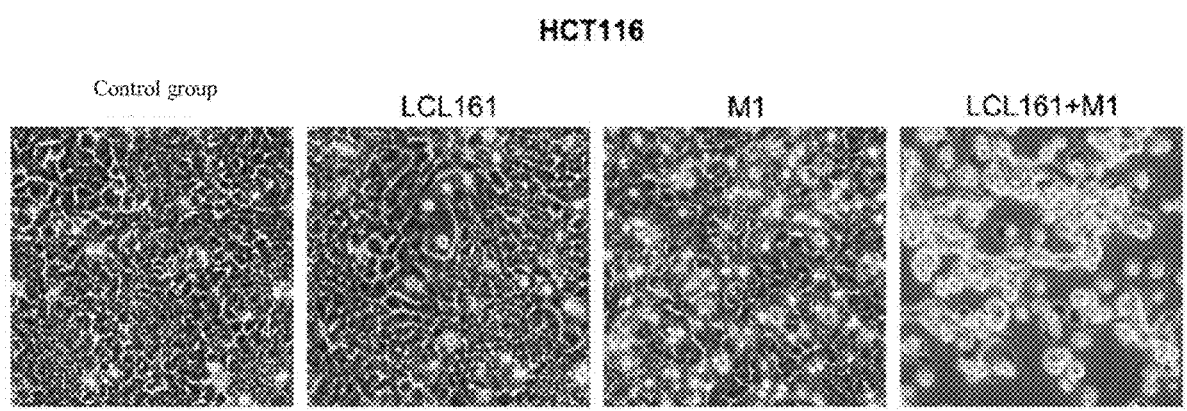
FIG. 1 shows that LCL161 and M1 virus significantly increase pathological changes in morphology of infected human colorectal cancer cells.

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the Sequence Listing:

SEQ ID NOs 1 and 2 are the respective sense and anti-sense strands of siRNA interference fragment 1 of cIAP1.

SEQ ID NOs 3 and 4 are the respective sense and anti-sense strands of siRNA interference fragment 2 of cIAP1. SEQ ID NOs 5 and 6 are the respective sense and anti-sense strands of siRNA interference fragment 3 of cIAP1.

SEQ ID NOs 7 and 8 are the respective sense and anti-sense strands of siRNA interference fragment 1 of cIAP2.

SEQ ID NOs 9 and 10 are the respective sense and anti-sense strands of siRNA interference fragment 2 of cIAP2.

SEQ ID NOs 11 and 12 are the respective sense and anti-sense strands of siRNA interference fragment 3 of cIAP2.

DETAILED DESCRIPTION

I. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Use of words such as "approximate", "about", "substantially", etc. modifies the value/description as would be understood by a person of skill in the art based upon the context and the parameter being described, and where further guidance is needed in order to be understood, a value of 5% can be applied. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." Described percent sequence identity refers to the percentage of nucleic acid or amino acid residues within a given DNA, RNA or protein, respectively, that are identical to the reference sequence.

In case of conflict, the present specification, including explanations of terms, will control. In addition, all the materials, methods, and examples are illustrative and not intended to be limiting.

II. Overview of Several Embodiments

Described herein is the use of a Caspase activator in the preparation of an anti-tumor synergist for oncolytic virus, wherein the oncolytic virus is selected from at least one alphavirus.

Described herein the use of a Caspase activator in the preparation of an anti-tumor synergist for oncolytic virus, wherein the oncolytic virus is selected from at least one alphavirus.

Preferably, the alphavirus is at least one selected from the group that includes M1 virus and Getah virus. M1 virus is a Getah-like virus, and it is reported that the homology of M1 virus and Getah virus is up to 97.8% in the relevant discovered viruses (Wen et al. Virus Genes. 2007; 35(3): 597-603).

For example, information about M1 virus and Getah virus can also refer to Chinese Patent 104814984A.

The alphavirus (e.g., M1 virus, Getah virus) described herein can include these existing oncolytic viruses as well as those viruses that may have undergone natural variation, or mutation (natural or forced or selective), or genetic modification, or addition or deletion of or substitution of portion(s) sequences. The oncolytic virus described herein includes those viruses that have undergone the above-described changes. Preferably said changes do not prevent said oncolytic viruses from exerting function recited in the present disclosure.

For example, the oncolytic virus may be the M1 virus as described in Genbank Accession No. EF011023, or may be a virus having a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EF011023.

In some embodiment, the oncolytic virus is M1 virus deposited with the China Center for Type Culture Collection on 17 Jul. 2014, and having a deposit number of CCTCC V201423. The oncolytic virus can also have a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide of said M1 with a deposit number of CCTCC V201423.

In other additional embodiments, the oncolytic virus may be a Getah virus as described in Genbank Accession No. EU015062, or may be a virus having a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EU015062.

In a particular embodiment, the oncolytic alphavirus is the M1 virus deposited with the China Center for Type Culture Collection on 17 Jul. 2014, and having a deposit number of CCTCC V201423 (see Chinese Patent 104814984A for detailed information of this strain).

In some embodiments of the described uses, the Caspase activator is at least one selected from the group consisting of Caspase-3, 7, 8, and 9 activators.

It will be understood that a Caspase activator is a composition, compound, substance, or agent that can increase the expression level of at least one of said Caspase, or that can increase the protein activity of at least one of said Caspase. In some embodiments, the Caspase activator is effective for, designed for, produced or raised using, or is specific for, Caspase 3 set forth in NCBI gene ID 836, or Caspase 7 set forth in NCBI Gene ID: 840, or Caspase 8 set forth in NCBI Gene ID:841, or Caspase 9 set forth in NCBI Gene ID: 842. In other embodiments, the Caspase activator is effective for, designed for, produced or raised using, or is specific for, a variant of the Caspase3 set forth in NCBI gene ID 836, or variant of the Caspase 7 set forth in NCBI Gene ID: 840, or variant of the Caspase 8 set forth in NCBI Gene ID:841, or variant of the Caspase 9 set forth in NCBI Gene ID: 842. The variant protein may have, for example, an amino acid sequence that is at least 80%, at least 85%, at least 90%, at least 91%, at least 92%, at least 93%, at least 94%, at least 95%, at least 96%, at least 97%, at least 98%, or at least 99%, identical to the said Caspase protein.

In some embodiments, a Caspase activator is a Caspase agonist. In some embodiments, a Caspase activator can be a Caspase disinhibitor. In some preferred embodiments, a Caspase activator can be an IAP inhibitor; preferably, the IAP inhibitor targets at least one IAP selected from the group including cIAP-1, cIAP-2 and XIAP.

In some embodiments, the IAP inhibitor is a substance for inhibiting the activity of IAP protein, a substance for degrading IAP protein, or a genetic tool for reducing the level of IAP protein. In particular embodiments, the substance for inhibiting the activity of IAP protein or the substance for degrading IAP protein is selected from the group including a protein or a compound. In particular embodiments, such compounds are selected from Smac protein or a Smac-like compound, such as LCL161 and Birinapant.

Other compounds that inhibit the activity of IAP protein, and which can be used as the IAP inhibitor described herein, include AT406 (SM-406), BV-6, SM-12d, GDC-0152, GDC-0197, SM-164, HGS 1029, LBW-242, WO2014060767, WO2014060768, WO2014060770, WO2014026882, JP1400, JP1201, JP1584, LBW242. Additional IAP inhibitors useable as described herein can be found in Rama Rathore (Apoptosis, 2017, 22: 898-919; incorporated by reference herein in its entirety).

In still further embodiments, the genetic tool for reducing the level of IAP protein is an RNA interference (RNAi) agent, microRNA, gene editing or gene knock-out material.

In a preferred embodiment of the present invention, the IAP protein inhibitor is an RNA interference fragment of IAP, or an antibody against IAP. In some embodiments, the IAP inhibitor is effective against, designed to target, produced or raised using, or is specific for, cIAP-1 set forth in NCBI Gene ID: 329, or cIAP-2 set forth in NCBI Gene ID: 330, or XIAP set forth in NCBI Gene ID: 331. In other embodiments, the IAP inhibitor is effective against, designed to target, produced or raised using, or is specific for, a variant of the cIAP-1 set forth in NCBI Gene ID: 329, or a variant of the cIAP-2 set forth in NCBI Gene ID: 330, or a variant of the XIAP set forth in NCBI Gene ID: 331. The variant protein may have, for example, an amino acid sequence that is at least 80%, at least 85%, at least 90%, at least 91%, at least 92%, at least 93%, at least 94%, at least 95%, at least 96%, at least 97%, at least 98%, or at least 99%, identical to the said IAP protein.

In some embodiments, the IAP inhibitor is an antibody. The antibody can be a monoclonal antibody, a polyclonal antibody, a multivalent antibody, a multispecific antibody (e.g., bispecific antibody), and/or an antibody fragment that binds to IAP. The antibody can be a chimeric antibody, a humanized antibody, a CDR-grafted antibody, or a human antibody, for example. The antibody fragment can be, for example, a Fab, Fab', F(ab')2, Fv, Fd, single chain Fv (scFv), disulfide bond Fv (sdFv), or a VL or a VH domain. The antibody can be in the form of a conjugate, for example, conjugated to a tag, a detectable label, or a cytotoxic agent. The antibody can be of the isotype IgG (e.g., IgG1, IgG2, IgG3 or IgG4), IgA, IgM, IgE or IgD.

The IAP inhibitor also includes, for example, small inhibitory nucleic acid molecules, such as short interfering RNA (siRNA), double-stranded RNA (dsRNA), micro-RNA (miRNA), ribozyme, and short hairpin RNA (shRNA), that decrease or ablate expression of IAP.

Such small inhibitory nucleic acid molecules can comprise a first and a second strand that hybridize to each other to form one or more double-stranded regions, each strand being about 18 to about 28 nucleotides in length, about 18 to about 23 nucleotides in length, or about 18, 19, 20, 21 or 22 nucleotides in length. Alternatively, a single strand may contain regions therein capable of hybridizing to each other to form a double-stranded region, such as in shRNA molecules.

Such small inhibitory nucleic acid molecules may also comprise modified nucleotides, while maintaining an ability to reduce or ablate IAP expression. The modified nucleotides may be included to improve in vitro or in vivo characteristics, such as stability, activity, and/or bioavailability. For example, such small inhibitory nucleic acid molecules may comprise modified nucleotides as a percentage of the total number of nucleotides present in the siRNA molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides). Such modified nucleotides may comprise, for example, deoxynucleotides, 2'-O-methyl nucleotides, 2'-deoxy-2'-fluoro nucleotides, 4'-thionucleotides, locked nucleic acid (LNA) nucleotides, and/or 2'-O-methoxyethyl nucleotides. The small inhibitory nucleic acid molecules, such as siRNAs, can also contain a '5- and/or a 3'-cap structure, to prevent degradation by exonucleases.

In some embodiments, the IAP inhibitor is a nucleic acid that is at least 90%, at least 91%, at least 92%, at least 93%, at least 94%, at least 95%, at least 96%, at least 97%, at least 98%, or at least 99% identical to the nucleic acids set forth as SEQ ID Nos 1-12.

In some embodiments, the small inhibitory nucleic acid molecules comprise double-stranded nucleic acids containing blunt ends, or overhanging nucleotides. Other nucleotides present may comprise, for example, nucleotides that result in mismatches, bulges, loops, or wobble base pairs. The small inhibitory nucleic acid molecules can be formulated for administration, for example, by encapsulation in liposomes, or by incorporation into other vehicles, such as biodegradable polymers, hydrogels, or cyclodextrins.

In some embodiments, the small inhibitory nucleic acid molecules comprise double-stranded nucleic acids containing blunt ends, or overhanging nucleotides. Other nucleotides present can comprise, for example, nucleotides that result in mismatches, bulges, loops, or wobble base pairs. The small inhibitory nucleic acid molecules can be formulated for administration, for example, by encapsulation in liposomes, or by incorporation into other vehicles, such as biodegradable polymers, hydrogels, or cyclodextrins.

Also described herein is a pharmaceutical composition for treating a tumor, including a (a) Caspase activator, including natural and synthetic Caspase activators; and (b) an oncolytic virus; wherein the oncolytic virus is selected from at least one alphavirus; such as the M1 virus or Getah virus. In particular embodiments, the Caspase activator is at least one selected from the group including Caspase-3, 7, 8, and 9 activators; which more preferably, is a Caspase disinhibitor;

and more preferably, is an IAP inhibitor. In some embodiments, the IAP inhibitor is at least one that targets an IAP selected from the group including cIAP-1, cIAP-2 and XIAP.

In particular embodiments of the described compositions, the IAP inhibitor is a substance, also described herein as an agent, for inhibiting the activity of IAP protein, a substance for degrading IAP protein, or a genetic tool for reducing the level, also described herein as the expression, of IAP protein.

In particular embodiments, the IAP inhibitor is an agent that is a natural or synthetic peptide, nucleic acid, or compound, such as a small molecule agent.

For example, in some embodiments, the substance for inhibiting the activity of IAP protein or the substance for degrading IAP protein is selected from the group including of a protein or a compound; such as a Smac protein or a Smac-like compound; such as LCL161 and Birinapant.

In particular embodiments, the IAP inhibitor is a genetic tool for reducing the level of IAP protein such as an RNAi agent, microRNA, gene editing or gene knock-out material.

Also described herein is a pharmaceutical kit for treating tumors, including (a) Caspase activator; and (b) oncolytic virus; the oncolytic virus is selected from at least one alphavirus; preferably, the alphavirus is at least one selected from the group including M1 virus and Getah virus. In the pharmaceutical kit, the Caspase activator and oncolytic virus are separately packaged; preferably, the Caspase activator is at least one of the Caspase-3, 7, 8 and 9 activators; more preferably, the Caspase activator is a Caspase disinhibitor; more preferably, the Caspase activator is IAP inhibitor; more preferably, the IAP is at least one selected from the group consisting of cIAP-1, cIAP-2 and XIAP.

In particular embodiments of the pharmaceutical kit, the IAP inhibitor is a substance for inhibiting the activity of IAP protein, a substance for degrading IAP protein, or a genetic tool for reducing the level of IAP protein; preferably, the substance for inhibiting the activity of IAP protein or the substance for degrading IAP protein is selected from the group including a protein or a compound; more preferably, the substance for inhibiting the activity of IAP protein or the substance for degrading IAP protein is selected from Smac protein or a Smac-like compound; or more preferably, the substance for inhibiting the activity of IAP protein or the substance for degrading IAP protein is at least one selected from the group including Smac-like compounds LCL161 and Birinapant; or more preferably, the genetic tool for reducing the level of IAP protein is an RNA interference agent, microRNA, gene editing or gene knock-out material.

Additionally provided herein is a use of the described combination of Caspase activator and oncolytic virus in the preparation of a medicament for treating tumor.

In various embodiments, the combination of Caspase activator and oncolytic virus can be used to treat various types of tumors. In particular embodiments of the described uses, pharmaceutical compositions, and kits, the tumor is a solid tumor or a blood tumor; preferably, said solid tumor is in or from a patient having liver cancer, colorectal cancer, bladder cancer, breast cancer, cervical cancer, prostate cancer, glioma, melanoma, pancreatic cancer, nasopharyngeal carcinoma, lung cancer, or gastric cancer. preferably, said tumor is a tumor that is not sensitive to said oncolytic virus; more preferably, said tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer, which is not sensitive to oncolytic virus. In a more preferred embodiment, the tumor is a tumor that is not sensitive to M1 oncolytic virus.

A single Caspase activator may be used, or several may be used in combination, concurrently or in series. The Caspase activator, and/or the oncolytic virus, may be in the form of compositions comprising one or more inhibitors, and one or more carriers, excipients, diluents, pharmaceutically-acceptable carriers, stabilizers, buffering agents, preservatives, non-ionic detergents, antioxidants, and other additives. The pharmaceutical composition can be administered to a patient by a variety of routes such as orally, transdermally, subcutaneously, intranasally, intravenously, intramuscularly, intrathecally, topically or locally. Typically, the Caspase activator will be administered orally, parenterally, intravenously or subcutaneously. The Caspase activator may be present in a composition together with the oncolytic virus, or they may be present in separate compositions.

The present disclosure also relates to methods for treating tumors. In some embodiments, one or more Caspase activator and one or more oncolytic viruses are administered to a subject having a tumor. The tumor may be a solid tumor or a blood tumor. Preferably, the solid tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer; preferably, the tumor is a tumor that is not sensitive to oncolytic virus; more preferably, the tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer, which is not sensitive to oncolytic virus. The Caspase activator may be administered concurrently, before, or subsequent to, administration of an oncolytic virus contemplated herein. Additionally, the Caspase activator and/or the oncolytic virus may be administered once a week, or several times (e.g., 2, 3, 4, 5, 6, 7, 8, 9 or 10) a week. The Caspase activator and/or the oncolytic virus may be administered for one or several weeks (1, 2, 3, 4, 5, 6, 7, 8, 9, or 10), for a month, or even for several months (2, 3, 4, 5, 6, 7, 8, 9, 10, 11 or 12 or more).

In a particular embodiment, the Caspase activator (e.g., LCL161 or Birinapant) and oncolytic virus are provided in a ratio of 0.01 to 15 mg: $10^3$-$10^9$ PFU; preferably 0.01-10 mg: $10^4$-$10^9$ PFU; more preferably 0.01-10 mg: $10^5$-$10^9$ PFU; and more preferably, the doses that are used are as follows: the Caspase activator (e.g., LCL161 or Birinapant)t is used in a range from 0.01 mg/kg to 15 mg/kg, while oncolytic virus is used in a titer such that MOI ranges from $10^3$ to $10^9$ (PFU/kg); preferably, the Caspase activator (e.g., LCL161 or Birinapant) is used in a range from 0.01 mg/kg to 10 mg/kg, while oncolytic virus is used in a titer such that MOI ranges from $10^4$ to $10^9$ (PFU/kg); more preferably, the Caspase activator (e.g., LCL161 or Birinapant) is used in a range from 0.1 mg/kg to 10 mg/kg, while oncolytic virus is used in a titer such that MOI ranges from $10^5$ to $10^9$ (PFU/kg).

In some particular embodiments, the provided pharmaceutical composition further comprises a pharmaceutically acceptable carrier. In other particular embodiments, the compositions are formulated for delivery as a lyophilized powder, injection, tablet, capsule, kit or patch.

Further provided herein are methods for treating a solid or hematological tumor in a subject, including administering to a subject in need thereof an oncolytic alphavirus as described herein; and a Caspase activator as described herein, thereby treating the tumor.

In some embodiments of the described methods, the Caspase activator is a IAP inhibitor including a nucleic acid, such as an DNA or RNAi agent, including siRNA, shRNA, microRNA, and the like. Particular examples of such RNAi agents include the nucleic acids set forth herein as SEQ ID NOs 1-12.

III. Anti-Tumor Combinations of a Caspase Activator and an Oncolytic Alphavirus Described herein is the discovery of an anti-tumor therapy using the combination of Caspase activator and alphavirus, which provides a surprising anti-tumor effect. It is known that Caspase activation causes cell apoptosis. The proteinases of the Caspase family are divided into three subgroups, in which Caspase-1, 4, 5 and 11 belong to the first subgroup; Caspase-2 and 9 belong to the second subgroup; and Caspase-3, 7, 8, and 10 belong to the third subgroup. The initial Caspase is cut and activated under the action of a foreign protein signal, the activated Caspase further cuts and activates the executor Caspase, and the activated executor Caspase further leads to programmed cell death (i.e. apoptosis) by hydrolyzing Caspase target protein.

In the combination therapies using an oncolytic virus and Caspase activation, the mechanism which results in the observed synergy is not yet clear. Nevertheless, it has been found that in some combinations, oncolytic virus and Caspase activator do not provide a synergistic pro-apoptotic effect, such as that described herein.

Preferably, the Caspase activator is at least one selected from the group consisting of Caspase-3, 7, 8 and 9 activators.

More preferably, the Caspase activator is a Caspase disinhibitor; more preferably, the Caspase activator is an IAP inhibitor; more preferably, the Inhibitor of Apoptosis (IAP) inhibitor is at least one selected from the group consisting of cellular inhibitor of apoptosis protein-1 (cIAP-1), cIAP-2 and x-linked inhibitor of apoptosis (XIAP).

As an alternative technical solution, the IAP inhibitor is a substance for inhibiting the activity of IAP protein, or a substance for degrading IAP protein, or a genetic tool for reducing the level of IAP protein, such substances, also referred to herein as an "agent" include natural or synthetic peptides (i.e. polypeptides or proteins), nucleic acids, including RNA interference agents, and compounds, such as small molecule biochemical modulators (inhibitors or activators).

Preferably, the substance for inhibiting the activity of IAP protein or the substance for degrading IAP protein is selected from a protein or a compound; more preferably, the substance for inhibiting the activity of IAP protein or the substance for degrading IAP protein is selected from second mitochondria-derived activator of caspases (Smac) protein or a Smac-like compound. More preferably, the substance for inhibiting the activity of IAP protein or the substance for degrading IAP protein is at least one selected from the group consisting of the Smac-like compounds LCL161 and Birinapant;

Or more preferably, the genetic tool for reducing the level of IAP protein is an RNA interference agent, microRNA, gene editing or gene knockout material. Examples of an RNA interference agent include siRNA, shRNA, and the like. Described herein are the siRNA agents set forth as SEQ ID NOs 1-12. Such agents and combinations thereof can be used in any of the uses, compositions, and methods described herein. Likewise, modifications of such agents that maintain their function can also be used. In particular examples, nucleic acids having at least 70%, 75%, 80%, 85%, 90%, 95%, or greater sequence identity (i.e. homology) to the described nucleic acids can be used.

The present disclosure also provides a pharmaceutical composition comprising the described Caspase activator and oncolytic alpha virus; or a pharmaceutical kit, in which IAP inhibitor and oncolytic virus are separately packaged. In particular embodiments, the Caspase activator is naturally-occurring. In other embodiments, the Caspase activator is synthetic, such as in any of the embodiments that use a RNAi agent, compound (or small molecule modulator), such as LCL161 and Birinapant and the like.

The pharmaceutical composition may also comprise a pharmaceutically acceptable carrier such as any carrier, filler, salt and the like as is standard in the art. In particular examples, the composition is formulated, along with standard pharmaceutical carriers, for administration or provision as a solution, lyophilized powder, injection, tablet, gel, capsule, caplet, kit patch, or any other delivery form standard to the art.

In particular embodiments, the Caspase activator and the oncolytic virus are provided in the same composition. In other embodiments, the Caspase activator and oncolytic virus are formulated separately. Likewise, both active agents can, in certain embodiments, be administered simultaneously, and in other certain embodiments, can be administered separately.

The uses, compositions, and methods described herein are direct towards anti-tumor therapy. In particular embodiments, the tumor may be a solid tumor. In other embodiments, the two is a hematological (blood) tumor.

Preferably, said solid tumor can be derived from or originate from a liver cancer, colorectal cancer, bladder cancer, breast cancer, cervical cancer, prostate cancer, glioma, melanoma, pancreatic cancer, nasopharyngeal carcinoma, lung cancer, or gastric cancer. In particular embodiments, any of the described tumors or cancer types can be or a type that is not sensitive to oncolytic virus, such as oncolytic alphavirus.

As described, in particular therapeutic embodiments, the Caspase activator can be a compound (e.g. small molecule), a protein, or a genetic tool.

Smac protein, having a full name of second mitochondria-derived activator of caspase (and abbreviated herein as Smac or SMAC), is present in mitochondria, and is conveyed from mitochondria to cytolymph upon apoptosis and regulates apoptosis-related pathways. Moreover, Smac (including Smac-like compounds) can enable or enhance tumor cell sensitivity to cellular factors like tumor necrosis factor (TNF)-α and TNF-related apoptosis-inducing ligand (TRAIL), thereby strengthening the paracellular effect of such factors. Smac is though to exert its function mainly by inhibiting the level and function of proteins of the IAP family. At present, there are 8 known types of IAP proteins, including cIAP-1, cIAP-2 and XIAP. IAP inhibits apoptosis by inhibiting the activation of caspase. IAP protein, is highly expressed in various tumors and is related to tumor development and poor prognosis. Thus, Smac (including Smac-like compounds) have been used for inhibiting IAP to produce an anti-tumor. However, as described herein, individual targeting of IAP produces a relative small anti-tumor effect in comparison to the provided combinations.

Combinations of a Smac-like compound and a further chemotherapeutic drug have been tested for treatment of pancreatic cancer. For example, Dineen et al. (Cancer Res. 2010; 70(7):2852-61) found that the combination of JP1021 (Smac-like compound) and Gemcitabine could significantly reduce the proliferation of cells. Therein, the cells treated without drugs had an apoptosis rate of 17%, and the cells treated with JP1021 (10 μmol/L) alone and the cells treated with Gemcitabine (10 μmol/L) alone had an apoptosis rate of 31% and 58% respectively. Also in contrast to the results presented herein, the combination of JP1021 and Gemcitabine did not have a synergistic effect, and induced an early apoptosis rate merely slightly higher than that obtained by using Gemcitabine alone.

The therapeutic effects of many compositions are difficult to predict. For example, the interactions between some drugs will reduce a desired therapeutic effect or cause undesired side effects. For some pharmaceutical compositions, the therapeutic efficacy of such composition is proved by comparison with combination of individual drugs, while for some pharmaceutical compositions, the synergistic effect is present if the therapeutic index of such composition is higher than that of combination of individual drugs.

The present disclosure firstly finds that a Caspase activator, e.g. IAP inhibitor, in combination with an oncolytic alphavirus, will have a synergistic effect, and can be used as an anti-tumor synergist for oncolytic alphavirus.

The inventor used interference fragments (siRNA) of cIAP1 and cIAP2 (SEQ ID Nos 1-12) to inhibit the expression of the two genes, thereby reducing the expression of the corresponding proteins. The results showed that interference and non-interference of cIAP1 and cIAP2 alone did not result in a pathological change of cell morphology, while using M1 virus alone also did not result in a pathological change of cell morphology. The interference of cIAP1 and cIAP2 in combination with infection with M1 virus significantly reduced the survival rate of cells. Thus, it was deduced that inhibition of cIAP1 and cIAP2 can significantly enhance the anti-tumor effect of oncolytic virus. Also demonstrated herein is that the IAP inhibitor—Smac-like compounds LCL161 and Birinapant—in combination with oncolytic virus, resulted in a synergistic anti-tumor effect.

It will be appreciated that the doses necessary to provide the expected effects described herein will be variable, depending on the subject to be treated and the agents being used.

In an exemplary embodiment, wherein oncolytic alphavirus is combined with LCL161 or Birinapant, the compound and oncolytic virus are provided in a ratio of 0.01 to 15 mg: $10^3$-$10^9$ PFU; including preferably 0.01-10 mg: $10^4$-$10^9$ PFU; and more preferably 0.01-10 mg: $10^5$-$10^9$ PFU.

In some embodiment: the Caspase activator (e.g., LCL161 or Birinapant) is used in a range from 0.01 mg/kg to 15 mg/kg, while oncolytic virus is used in a titer such that MOI ranges from $10^3$ to $10^9$ (PFU/kg). In some preferred embodiments, the Caspase activator (e.g., LCL161 or Birinapant) is used in a range from 0.01 mg/kg to 10 mg/kg, while oncolytic virus is used in a titer such that MOI ranges from $10^4$ to $10^9$ (PFU/kg). In some other embodiments, the Caspase activator (e.g., LCL161 or Birinapant) is used in a range from 0.1 mg/kg to 10 mg/kg, while oncolytic virus is used in a titer such that MOI ranges from $10^5$ to $10^9$ (PFU/kg).

It will be appreciated that the agents, such as the compounds described herein (including small molecule compounds) can be obtained through, but not limited to, chemical separation or synthesis per se or other standard commercial approaches.

As an exemplary embodiment, the Caspase activator may also be interference RNA fragments of cIAP1 and cIAP2, including but not limited to those RNAi agents described herein as SEQ ID NOs 1-12.

The oncolytic virus (for example alphavirus such as M1 virus and Getah virus) described herein may particularly refer to the existing oncolytic viruses, but the viruses that may undergo natural variation, or undergo mutation, modification, addition or deletion of sequences may not be excluded. The oncolytic viruses which undergo changes such as variation, mutation, modification, addition or deletion of sequences that do not affect the effects of said oncolytic virus as described in the present disclosure belong to the homogenous virus described in the present disclosure.

In other embodiments, the described IAP inhibitor is the agent (substance, for example, compounds, amino acid sequences, or nucleotide sequences) or tool for reducing, knocking down or otherwise affecting the gene expression of IAP or reducing the protein amount or protein activity of IAP. Accordingly it should be understood that the agents described can function to inhibit IAP expression at the transcriptional or translational level. In an additional embodiment, such agents could act post-translationally and affect the stability of the IAP protein itself. Those skilled in the art could modify, replace and change these compounds, amino acid sequences or genetic tools. Provided that the resulting substance has the effect of inhibiting IAP, such substances and agents can be used as described herein and, and can serve as an equivalent replacement of the above compounds, amino acid sequences and tools that are expressly described.

The present invention also provides a pharmaceutical composition or a pharmaceutical kit. The pharmaceutical kit differs from the composition in that in the pharmaceutical kit, the Caspase activator (or the derivative thereof or the combination thereof) is not necessarily and not usually mixed with oncolytic virus, but is generally packaged separately. Oncolytic virus and Caspase activator that are separately packaged may also comprise a respective adjuvant. Such adjuvants include a means that could aid the therapeutic effect of a pharmaceutical drug. A pharmaceutical kit may also comprise Caspase activator or the derivative thereof or the combination thereof and oncolytic virus that are packaged individually.

The Caspase activator or the derivative thereof or the combination thereof and oncolytic viruses as described herein, including in the pharmaceutical kit, may be administered simultaneously or in any order, which comprises firstly administering one drug to a patient, and then administering the other drug to the patient. Said patient refers to a mammal subject, especially human, such as a patient in need of the therapeutic treatments described herein.

Further provided herein are methods for treating a solid or hematological tumor in a subject, including administering to a subject in need thereof an oncolytic virus as described herein; and a Caspase activator as described herein, thereby treating the tumor. The oncolytic virus and Caspase activator for use in the described methods can be any virus or activator as described in the above uses, compositions, and kits. As indicated above, the virus and Caspase activator can be administered in separate or combined formulations as are standard in the art. It will be appreciated that solid and liquid forms of the described agents are within the scope of this disclosure. As are local and systemic modes of administration. It is noted that in particular examples a local form of administration can include methods commonly used for systemic administration (such as injection and the like). It will also be appreciated that the method of treatment described herein do not require that the disappearance of the tumor to be treated. Any effect deemed to be therapeutic is understood to be included in the present understanding of treatment.

In the present disclosure, it is found that a Caspase activator, for example, LCL161 and Birinapant, can enhance the anti-tumor effect of oncolytic virus, so as to improve the therapeutic efficacy of oncolytic alphavirus as an anti-tumor drug. For example, cytological experiments prove that M1 virus in combination with LCL161 and Birinapant respectively can remarkably cause the pathological change of tumor cells in terms of morphology, which significantly inhibit tumor cell growth.

The inventor applied LCL161 or Birinapant in combination with M1 virus to human colorectal cancer HCT116 cell strain, and surprisingly found that when antiviral compound LCL161 was used in combination with M1 virus, the pathological change of tumor cells in terms of morphology was significantly increased, and the survival rate of tumor cells was significantly reduced. In some cases, the morphological change in tumor cells included cell swelling, nuclear condensation and fragmentation with cells then undergoing apoptosis. For example, in an example of the present invention, and as described in greater detail below, when M1 virus (MOI=0.001) alone was used for treating colorectal cancer HCT116 cells, the tumor cells had a survival rate of 84%, and when 5 μm of LCL161 was used in combination with M1 virus having the same MOI, the survival rate of the tumor cells was sharply reduced to 21.6%. Thus, compared with the anti-tumor effect of M1 virus alone, the combination of LCL161 and M1 produced a significantly improved oncolytic effect.

Chinese patent CN 201510990705.7 previously submitted by the inventor disclosed that EGFR inhibitor chrysophanol and the derivative thereof can be used as anti-tumor synergists for M1 virus, and a combination of both could reduce the survival rate of tumor cells to 39.6%. Specifically, it was disclosed that when 50 μM chrysophanol was used in combination with M1 virus (MOI=0.001), liver cancer cell strain Hep3B may be significantly killed. However, disclosed herein is a lower concentration of Caspase activator used in combination with alphavirus, while an even more reduced survival rate of tumor cells was found. In addition, the tumor cell used in the present disclosure is even less sensitive compared to the tumor cell Hep3B which is used in CN 201510990705.7. In the present disclosure, when 50l LCL161 was used in combination with M1, colorectal cancer cell strain HCT 116 may be significantly killed. Actually, as compared with Hep3B (the survival rate of cells after treatment with 0.01 MOI was 85.1%) cells, HCT116 cells were even less sensitive to M1 cells (the survival rate of the cells after treatment with 10 MOI was 84.0%). Obviously, as compared with chrysophanol, the present disclosed anti-tumor synergist for M1 could significantly improve the killing effect on non-sensitive tumors. Meanwhile, LCL161 was used in a dose that was merely a tenth of chrysophanol, and had significant advantages.

Although LCL161 per se is reported to produce anti-tumor effect by inhibiting the proteins cIAP1 and cIAP2 that inhibit apoptosis in tumor cells, it is found in the present disclosure that a combination use of Caspase activator, such as LCL161, and alphavirus, can significantly increase the killing effect on tumor cells, compared with a use of Caspase activator alone, such as LCL161, at the same concentration. For example, when tumor cells were treated with 5 μM LCL161, the tumor cells had a survival rate of up to 92.6%, and for example when 5 μM LCL161 was used in combination with M1 virus, the survival rate of the tumor cells was sharply reduced to 33.6%. Clearly, the greatly enhanced oncolytic effect produced by the combination of LCL161 and M1 benefits from the synergistic mechanism between LCL161 and M1 virus, rather than the function produced by the anti-tumor mechanism of LCL161.

The important significance of the present disclosure also lies in that for some tumors that are less sensitive to drugs, the particular combination therapy provided in the present disclosure provides a reliable and effective therapy for the treatment of such tumors.

The following examples are provided to illustrate certain particular features and/or embodiments. These examples should not be construed to limit the disclosure to the particular features or embodiments described.

Unless otherwise specified, the materials and experimental methods used in the present disclosure are conventional materials and methods.

EXAMPLES

Example 1: LCL161 and M1 Virus Significantly Increase the Pathological Changes in Morphology of Human Colorectal Cancer Cell Lines Materials Human colorectal cancer cell line HCT116 (purchased from ATCC), M1 virus (obtained with CCTCC V201423), a high glucose-containing DMEM culture medium, (4.5 g/l glucose) (purchased from Corning) and an inverted phase contrast microscope.

Methods:

a) Cultivation of cells: Human colorectal cancer cell line HCT116 was grown in a DMEM complete culture medium containing 10% FBS, 100 U/ml penicillin and 0.1 mg/ml streptomycin; all cell cultures were placed in a closed incubator with 5% $CO_2$ at 37° C. constant temperature (relative humidity 95%) for subculture. Growth of the cultured cells was observed by phase contrast microscopy. Cells were passaged about every 2-3 days, and the cells in exponential growth phase were used in the described assays.

b) Cell treatment and morphological observation: The cells in exponential growth phase were selected and added into a DMEM complete culture medium (containing 10% fetal bovine serum, 1% penicillin/streptomycin (Life Technologies)) to prepare a cell suspension. The cells were inoculated into a 24-well culture plate at a density of $2.5 \times 10^4$/well. 72 hours after, the cells were treated with LCL161 (5 μM) alone, infected with M1 virus (M01=0.01), or treated with a combination of M1 virus (MOI=0.01) and LCL151 (5 μM), morphological changes were observed by inverted phase contrast microscopy, and using an untreated culture as the control group.

Results

As shown in FIG. 1, the morphology of the cells was observed by the phase-contrast microscope. HCT116 cells were grown in adherent monoculture, and the cells were closely arranged with a uniform phenotype. 72 hours after the treatment with LCL161 (5 μM) and M1 virus (MOI=1), the morphology of the cells was significantly changed. As compared with the cells in the control group, the cells in the group treated with M1 alone, and the cells in the group treated with LCL161 alone, the number of the cells in the combined treatment group was significantly deceased, the cell body was contracted to a spherical shape, the refractive index was significantly increased, and the cells showed pathological changes indicating cell death.

Example 2. Combined Treatment with LCL161/Birinapant and M1 Virus Significantly Decreases the Survival Rate of Human Colorectal and Liver Cancer Cells Materials Human colorectal cancer cell line HCT116, SW480, human liver cancer cell line Huh7, PLC, M1 virus, a high glucose-containing DMEM culture medium, and an automatic microplate reader for enzyme-linked immunosorbent assay. Cells and virus, are from the same sources as Example 1.

Methods a) Inoculation of cells and administration treatment: cells in the exponential growth phase were selected and added into a DMEM complete culture medium (containing 10% fetal bovine serum and 1% penicillin/streptomycin (Life Technologies)) to prepare a cell suspension. The cells were inoculated into a 96-well culture plate at a density of $4 \times 10^3$/well. After 12 hours, the cells were completely adherent to the wells. The experiment was divided into a control group and a single drug group (using 5 µM LCL161 or Birinapant alone), a group infected with M1 and a group treated with LCL161/M1 or Birinapant/M1. In M1-containing assays, virus was provided at varying MOI. The concentration of LCL161 or Birinapant was 5 µM b) Reaction of MTT with succinate dehydrogenase in the cells: 72 hours after culture, 20 µl MTT (5 mg/ml) was added into each well, and was incubated for a further 4 hours. After incubation, granular blue and purple formazan crystals formed in the living cells were observed by microscopic examination.

c) Dissolution of formazan particles: those cultures having cells with formazan crystals were further processed as follows. Supernatant was carefully sucked off from the cultures, 100 µl/well DMSO was added to dissolve the formed crystals, and the culture plates were shaken in a microoscillator for 5 minutes. The optical density (OD value) of each well was detected in an enzyme linked detector at a wavelength of 570 nm. The experiments were repeated for 3 times for each group. The calculated survival rate of the cells=OD value of the drug treatment group/OD value of the control group× 100%.

Results

Figure 2A:
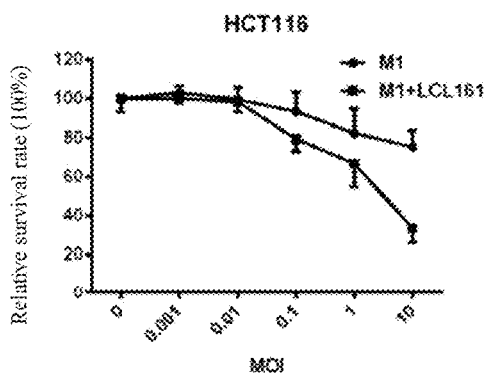
FIGS. 2(A) to 2(H) show that combined treatment of LCL161/Birinapant and M1 virus significantly reduces the survival rate of human colorectal and liver cancer cell lines.
Figure 2B:
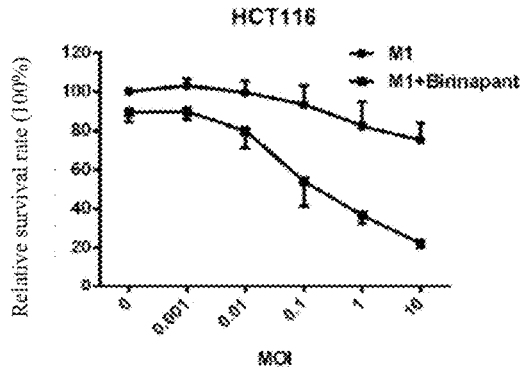
Figure 2C:
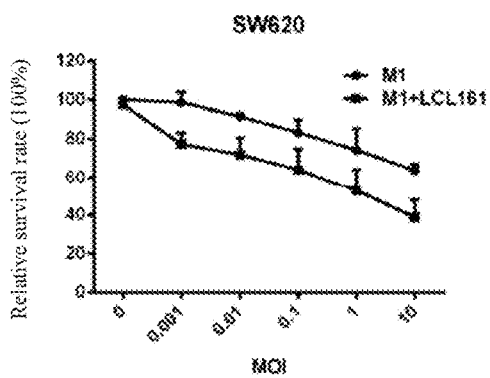
Figure 2D:
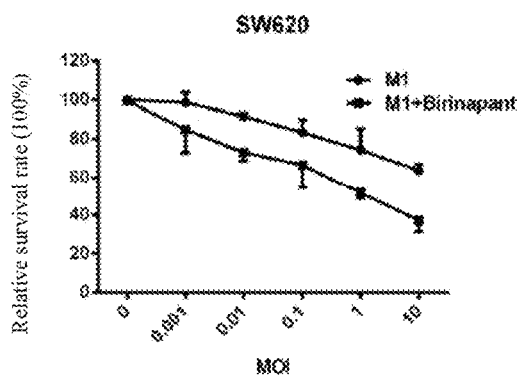
Figure 2E:
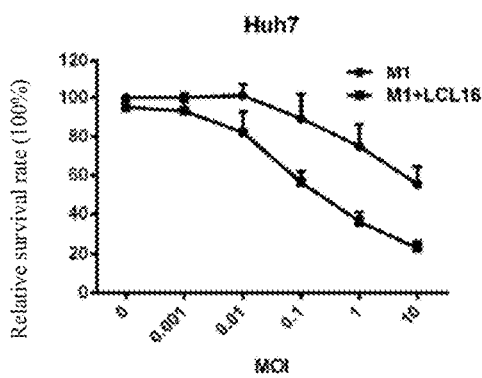
Figure 2F:
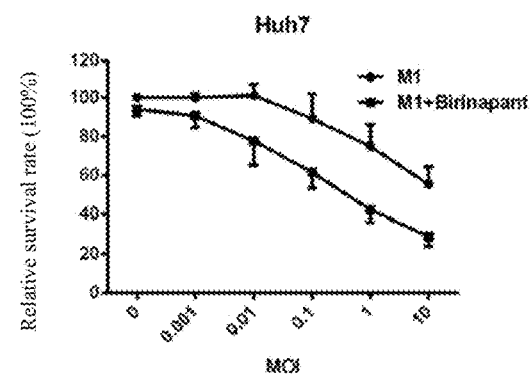
Figure 2G:
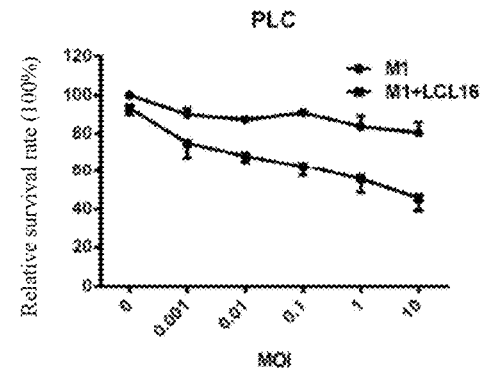
Figure 2H:
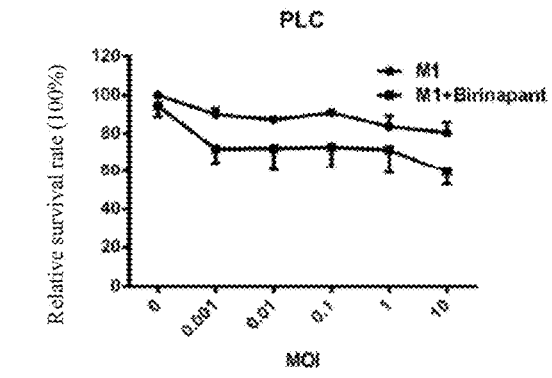

As shown in FIG. 2(A), treatment with M1 virus alone reduced the survival rate of tumor cell line HCT116 (84.0%). Tumor cells treated with 5 µM LCL161 had a survival rate of up to 92.6%. In contrast, tumor cells treated with the combination of M1 and LCL161 (M1+LCL161) showed a significantly decreased a survival rate of 33.6%. Likewise, as compared with the group treated with M1 virus alone or the group treated with LCL161 alone, the tumor cells treated with the combination of LCL161/M1 at various doses had a significantly reduced survival rate. Similar results were observed for HCT116 in the group treated with the combination of Birinapant/M1 (FIG. 2B). Additionally, the combination of LCL161 or Birinapant and M1 also significantly reduced the survival rate of tumor cells SW620 (FIGS. 2(C) and 2(D)), Huh7 cells (FIGS. 2(E) and 2(F)), and PLC cells (FIGS. 2(G) and 2(H)).

Example 3: Anti-Tumor Effect Achieved by the Inhibition of cIAP1 and cIAP2 in Combination with Infection by M1 Oncolytic Virus Materials M1 virus, human colorectal cancer cell line HCT116, liver cancer cell line Huh7, RNA interference fragments of cIAP1 and cIAP2, MTT (methyl thiazolyl tetrazolium) (purchased from MPbio), and a phase contrast microscope. Cells and virus are from the same sources as Example 1.

Methods

The cells in the exponential growth phase were selected and added into a DMEM complete culture medium to prepare a cell suspension. The cells were inoculated into a 6-well plate at a density of $1 \times 10^5$/well. After 24 hours, a siRNA target gene fragment in liposomes was added, as indicated in FIGS. 3(A) to 3(D), and as described herein as SEQ ID NOs 1-12. After 48 hours, the cells were infected with M1 virus. 48 hours after infection, the samples were treated as follows:

(1) A portion of the cells were harvested and protein isolated. RNA interference efficiency was detected by Western blot.

(2) The survival rate of the cells was calculated by MTT assay as described above.

Results

Respective interference of cIAP1 and cIAP2 with different interference fragments was measured by Western blot detection of IAP protein. It was found that at least two siRNA fragments could cause a significant decrease in the expression of cIAP1 and cIAP2 proteins (FIGS. 3(A) and 3(B)). This demonstrates that an RNAi interference fragment could interfere the expression of cIAP1 and cIAP2 proteins at the level of translation.

Figure 3A:
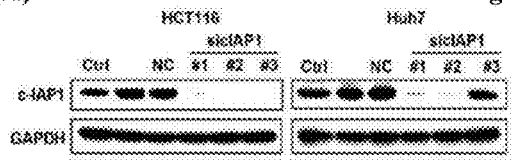
FIGS. 3(A) to 3(D) show the anti-tumor mechanism of LCL161 in combination with oncolytic virus.
Figure 3B:
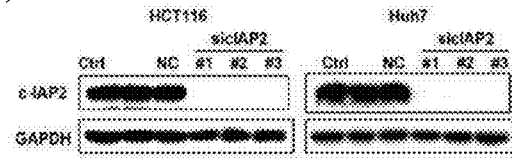
Figure 3C:
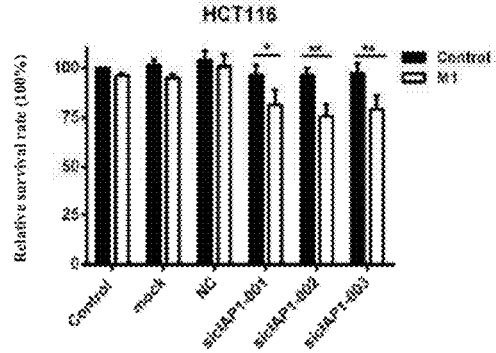
Figure 3C:
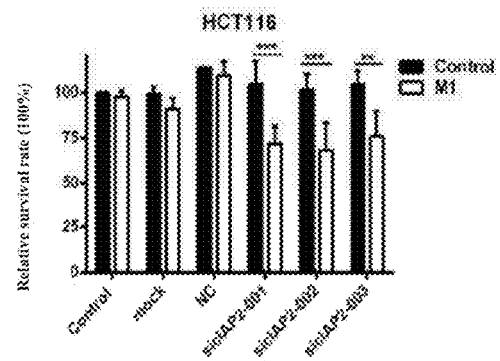
Figure 3D:
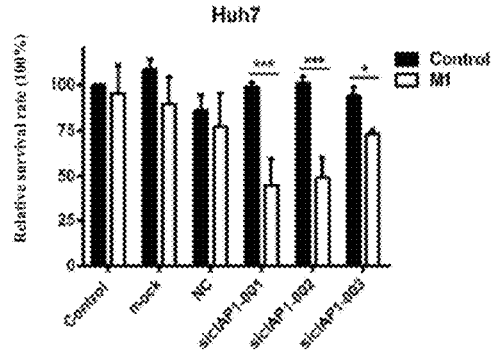
Figure 3D:
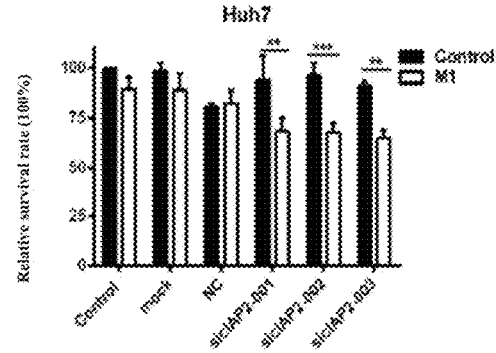

In FIGS. 3(C) to 3(D), control refers to the control group, i.e. a group without treatment, mock refers to a group using a transfection reagent alone (RNAiMAX), NC refers to a group with a scrambled siRNA interference fragment, and the last three columns refer to the cells whose expression is inhibited by siRNA fragments.

MTT assay of treated cells demonstrated that the group with RNA interference of cIAP1 and cIAP2 alone, as compared with the non-interference group (control group) or the group with scrambled interference (NC), does not change tumor cell survival rate. Meanwhile, the infection with M1 virus alone also did not the cellular survival rate In contrast, RNA interference of cIAP1 or cIAP2 in combination with the infection with M1 significantly reduced the survival rate of tumor cells (FIGS. 3(C) and 3(D)). The data was subject to ANOVA statistics (wherein * indicates $p<0.05$,  indicates $p<0.01$, * indicates $p<0.001$), which showed that there was statistical significance in the decrease of the survival rate of the cells.

These results indicate that the inhibition of cIAP1 and cIAP2 in combination with the application of M1 virus produce an anti-tumor effect.

Example 4. The Combination of LCL161 and M1 Virus Significantly Inhibits the Growth of Transplantable Tumors of Human Colorectal and Liver Cancer Cell Lines Materials M1 virus, colorectal cancer cell line HCT116, liver cancer cell line Huh7, 4-week-old female BALB/c nude mice (Model animal research center of Nanjing University). Cells and virus are from the same sources as Example 1.

Methods

The present experiment was performed as a randomized and single-blinded trial. $5 \times 10^6$ HCT116 or $1 \times 10^7$ Huh7 cells were subcutaneously injected into dorsa of 4-week-aged BALB/c nude mice. When the size of tumors reached 50 mm$^3$, the mice were divided into groups, including an untreated control group (Control), a group treated with LCL161 alone (i.p. 20 mg/kg/d), a group infected with M1 alone (transplantable tumor of HCT116 cancer strain was injected with M1 virus via tail vein ($2 \times 10^6$ PFU/time), and transplantable tumor of Huh7 cancer strain was injected with M1 virus via tail vein ($5 \times 10^5$ PFU/time)) and a group treated with LCL161/M1 (LCL161 and M1 virus were administered in the same way at the same dose), and four injections was performed continuously (for HCT116, injection was conducted on day 5, day 6, day 7, and day 8; for Huh7, injection was conducted on day 10, day 11, day 12, and day 13). The weight, length and width of the tumor were measured every two days, and the volume of the tumor was calculated according to the formula: (length×width$^2$)/2. After measuring the volume of the tumor, one way ANOVA statistics was carried out, wherein * indicates p<0.001,  indicates p<0.01, and * indicates p<0.05.

Results

Figure 4A:
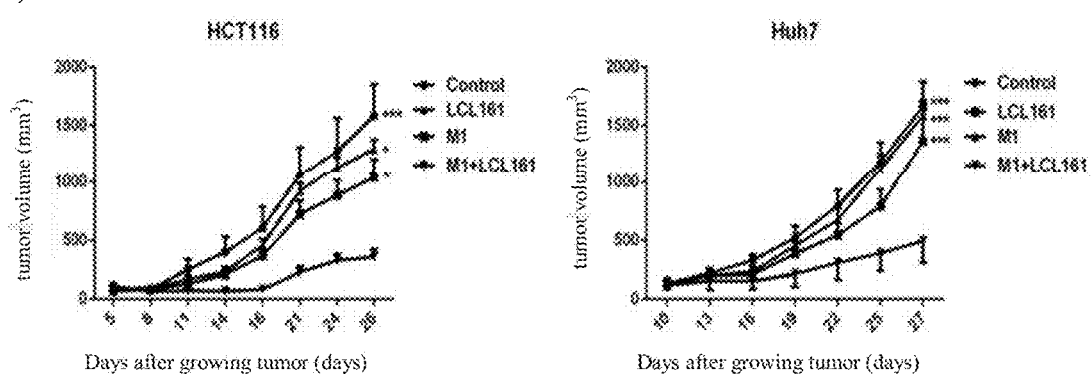
FIGS. 4(A) and 4(B) show that combined treatment with LCL161 and M1 virus significantly inhibits the growth of transplantable tumors of human liver (right panels) and colorectal (left panels) cancer cell lines.
Figure 4B:
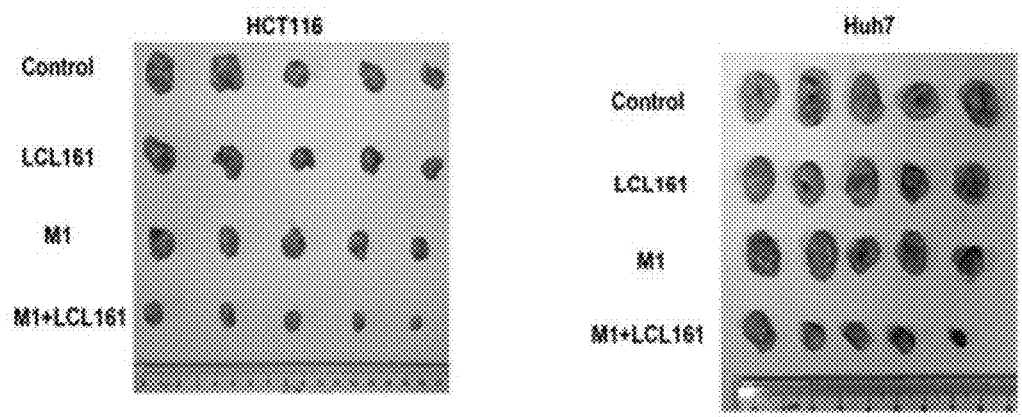
Figure 5A:
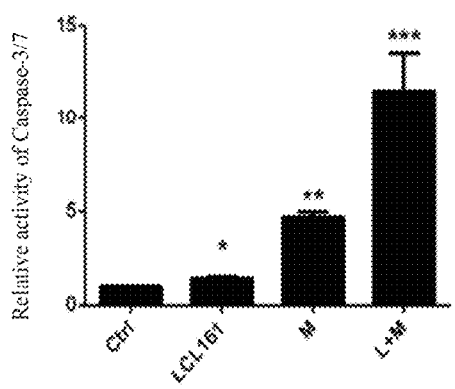
FIGS. 5(A) to 5(F) show that the combination of LCL161 and M1 virus significantly up-regulates the activities of caspase-3/7, 8 and 9 in human colorectal and liver cancer cell lines.
Figure 5B:
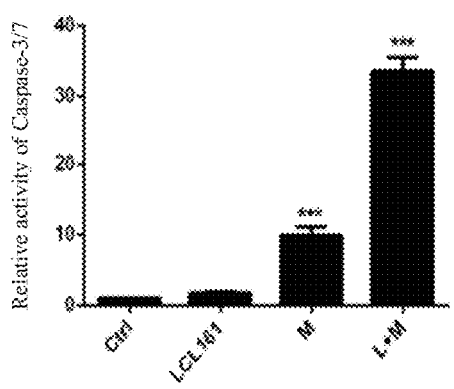
Figure 5C:
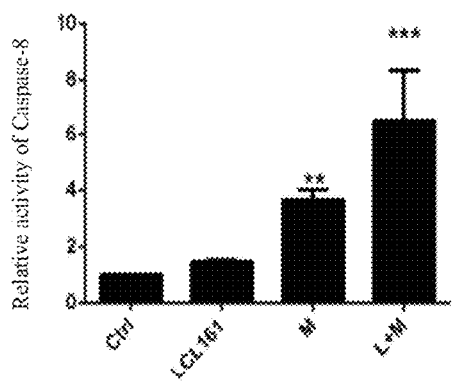
Figure 5D:
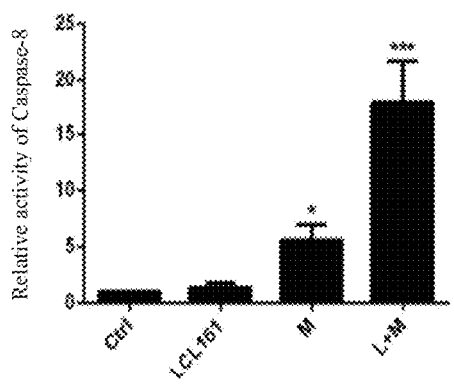
Figure 5E:
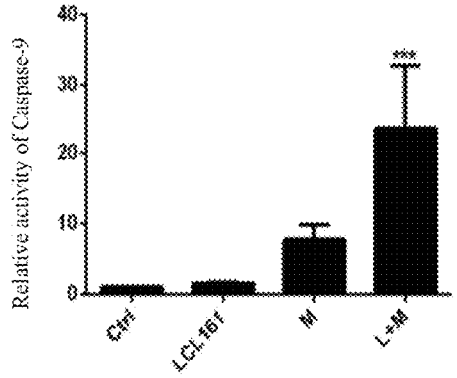
Figure 5F:
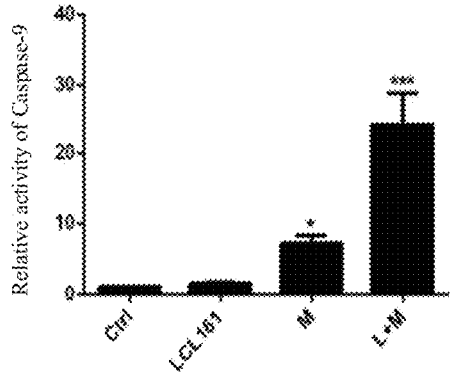

Pathology studies on the tumor-implanted animals were carried out to determine tumor volume. The results showed that as compared with the control group, the group treated with LCL161 alone and the group infected with M1 alone resulted in only a slight reduction in tumor volume (FIGS. 4(A) and 4(B), left panels).

In animals inoculated with HCT116 tumors: the LCL61 treatment group, as compared with the control group, demonstrated a reduction in tumor volume of only 29.15%. The M1 treatment group, as compared with the control group, demonstrated a reduction in tumor volume of only 27.93%. In contrast, the combined treatment with LCL161/M1 induced a significant reduction in tumor volume (FIGS. 4(A) and 4(B), left panels), As compared with the control group, the combined treatment resulted in a decrease in tumor volume of 80.42%.

Similarly, in animals inoculated with Huh7 tumors, the LCL161 treatment group, as compared with the control group, reduced tumor volume only by 18.1%, and the M1 treatment group, as compared with the control group, reduced tumor volume only by 4.7%. In contrast, the combined treatment of LCL161/M1 resulted in a significant reduction in tumor volume (FIGS. 4(A) and 4(B), right panels). As compared with the control group, the combined treatment resulted in a decrease in tumor volume of 70.3%. As shown in the figures, one way ANOVA statistics indicate the statistical significance of the presented data.

Example 5. The Combination of LCL161 and M1 Virus Significantly Up-Regulates the Activities of Caspase-3/7, 8 and 9 of Human Colorectal and Liver Cancer Cell Lines Materials M1 virus, LCL161, a kit for detecting the activities of Caspase 3/7/8/9 (purchased from Promega: Caspase3/7 G8091; Caspase 8 G8201; Caspase 9 G8211), a DMEM complete culture medium (containing 10% fetal bovine serum, 1% penicillin/streptomycin (Life Technologies)), colorectal cancer cell line HCT116, liver cancer cell line Huh7, and an automatic microplate reader for enzyme-linked immunosorbent assay. Cells and virus are from the same sources as Example 1.

Methods

The cells in the exponential growth phase were selected and added into a DMEM complete culture medium (containing 10% fetal bovine serum and 1% penicillin/streptomycin (Life Technologies)) to prepare a cell suspension. The cells were inoculated into a 96-well culture plate at a density of $4 \times 10^3$/well. After 12 hours, the cells were completely adherent to the walls of the culture plate. In this experiment, cultures were divided into a control group, a single drug group (using LCL161 alone), a group infected with M1, and a group treated with combined LCL161/M1. The doses used were as follows: cells were infected with M1 at 1 MOI (HCT161 cells) or 0.1 MOI (Huh7 cells), and LCL161 was added at a concentration of 5 µM. Each of the above mentioned treatment groups was divided in four for detecting MTT and the activities of Caspase 3/7, 8 and 9. 72 hours after treatment, the reagent for detecting Caspase3/7, 8 and 9 was added into each well on the basis of the volume, and the resulting wells were placed into the incubator for a further half hour. The liquid was absorbed into the opaque 96 well plate for measuring the chemical luminous intensity by a microplate reader. Meanwhile, MTT was detected to calculate the survival rate of the cells. The activity of Caspase was standardized by the ratio of chemiluminescent value to MTT value.

Results

As shown in FIGS. 5(A) to 5(F), the detected activities of Caspase3/7, 8 and 9 indicated that in HCT116 cells and Huh7 cells, and as compared with the control group (Ctrl), the cells treated with LCL161 or M1 (M) alone only slightly up-regulated the activities of Caspase 3/7, 8, and 9. In contrast, the group treated with the combination of LCL161 and M1 (LM) showed significant up-regulation in the activities of Caspase3/7, 8, and 9 (FIGS. 5(A) to 5(F)). These observations demonstrate that Caspase active agent, i.e., the combination of LCL161 and M1, could significantly activate the activities of Caspase 3/7, 8, and 9.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a solid or hematological tumor in a subject, comprising: administering to a subject in need thereof at least one of M1 virus or Getah virus; and enhancing an anti-tumor effect of said M1 or Getah virus comprising administering to the subject in need thereof at least one Inhibitor of Apoptosis (IAP) inhibitor.

2. The method of claim 1, wherein the solid tumor is of a cancer selected from the group consisting of liver cancer, colorectal cancer, bladder cancer, breast cancer, cervical cancer, prostate cancer, glioma, melanoma, pancreatic cancer, nasopharyngeal carcinoma, lung cancer, and gastric cancer.

3. The method of claim 1, wherein the IAP inhibitor is LCL161 or Birinapant, and the LCL161 or Birinapant and said M1 or Getah virus are provided in a ratio of 0.01 to 15 mg:$10^3$-$10^9$ PFU.

4. The method of claim 1, wherein the M1 or Getah virus and IAP inhibitor are provided as a pharmaceutical composition further comprising a pharmaceutically acceptable carrier.

5. The method of claim 1, wherein the IAP is at least one selected from the group consisting of cIAP-1, cIAP-2 and XIAP.

6. The method of claim 1, wherein the IAP inhibitor is a Smac protein.

7. The method of claim 1, wherein the TAP inhibitor is used in a range from 0.01 mg/kg to 15 mg/kg, while said M1 virus or Getah virus is used in a titer such that MOI ranges from $10^3$ to $10^9$ (PFU/kg).

8. The method of claim 1, wherein the TAP inhibitor is used in a range from 0.1 mg/kg to 10 mg/kg, while said M1 virus or Getah virus is used in a titer such that MOI ranges from $10^5$ to $10^9$ (PFU/kg).

9. The method of claim 1, wherein the M1 virus or Getah virus is an M1 virus.

10. The method of claim 1, wherein said M1 virus or Getah virus has a genome as described in Genbank Accession No. EF011023, or has a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EF011023.

11. The method of claim 1, wherein said M1 virus or Getah virus has at least 80%, at least 85%, at least 90%, at least 91%, at least 92%, at least 93%, at least 94%, at least 95%, at least 96%, at least 97%, at least 98%, or at least 99% nucleotide sequence identity to the genome of the M1 virus deposited under Accession No. CCTCC V201423.

12. The method of claim 1, wherein said M1 virus or Getah virus has at least 97.8% nucleotide sequence identity to the genome of the M1 virus deposited under Accession No. CCTCC V201423.

13. The method of claim 1, wherein said M1 virus or Getah virus is the M1 virus deposited under Accession No. CCTCC V201423.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence

```
<220> FEATURE:
<223> OTHER INFORMATION: Synthetic sequence

<400> SEQUENCE: 1
gugaguucuu gauacgaaud tdt                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic sequence

<400> SEQUENCE: 2
auucguauca agaacucacd tdt                                              23

<210> SEQ ID NO 3
<211> LENGTH: 23
<212> TYPE: DNA
<213> ORGANISM: Artificial Sequence
<220> FEATURE:
<223> OTHER INFORMATION: Synthetic sequence

<400> SEQUENCE: 3
gaauacgucu ccaaugagad tdt                                              23

<210> SEQ ID NO 4
<211> LENGTH: 23
<212> TYPE: DNA
<213> ORGANISM: Artificial Sequence
<220> FEATURE:
<223> OTHER INFORMATION: Synthetic sequence

<400> SEQUENCE: 4
ucucauugga gacguauucd tdt                                              23

<210> SEQ ID NO 5
<211> LENGTH: 23
<212> TYPE: DNA
<213> ORGANISM: Artificial Sequence
<220> FEATURE:
<223> OTHER INFORMATION: Synthetic sequence

<400> SEQUENCE: 5
gcaagugcug gauucuauud tdt                                              23

<210> SEQ ID NO 6
<211> LENGTH: 23
<212> TYPE: DNA
<213> ORGANISM: Artificial Sequence
<220> FEATURE:
<223> OTHER INFORMATION: Synthetic sequence

<400> SEQUENCE: 6
aauagaaucc agcacuugcd tdt                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic sequence

<400> SEQUENCE: 7
gauugugcuc cuucuuuaad tdt                                              23
```

```
<210> SEQ ID NO 8
<211> LENGTH: 23
<212> TYPE: DNA
<213> ORGANISM: Artificial Sequence
<220> FEATURE:
<223> OTHER INFORMATION: Synthetic sequence

<400> SEQUENCE: 8
uuaaagaagg agcacaaucd tdt                                              23

<210> SEQ ID NO 9
<211> LENGTH: 23
<212> TYPE: DNA
<213> ORGANISM: Artificial Sequence
<220> FEATURE:
<223> OTHER INFORMATION: Synthetic sequence

<400> SEQUENCE: 9 gauauuccg uggcucuuad tdt                                               23

<210> SEQ ID NO 10
<211> LENGTH: 23
<212> TYPE: DNA
<213> ORGANISM: Artificial Sequence
<220> FEATURE:
<223> OTHER INFORMATION: Synthetic sequence

<400> SEQUENCE: 10
uaagagccac ggaaauaucd tdt                                              23

<210> SEQ ID NO 11
<211> LENGTH: 23
<212> TYPE: DNA
<213> ORGANISM: Artificial Sequence
<220> FEATURE:
<223> OTHER INFORMATION: Synthetic sequence

<400> SEQUENCE: 11
gauugugcuc cuucuuuaad tdt                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic sequence

<400> SEQUENCE: 12
uuaaagaagg agcacaaucd tdt                                              23
```